United States Patent [19]
Kojima et al.

[11] 4,030,837
[45] June 21, 1977

[54] METHOD AND APPARATUS FOR AUTOMATICALLY MEASURING DISTRIBUTION OF REFLECTANCE OF COALS

[75] Inventors: Kojiro Kojima, Kunitachi; Yoshihisa Sakurai, Yokohama; Tetuya Sugai, Tokyo; Masayoshi Motegi, Yokohama, all of Japan

[73] Assignee: Nippon Steel Corporation, Tokyo, Japan

[22] Filed: Sept. 29, 1975

[21] Appl. No.: 617,490

[52] U.S. Cl. .............................. 356/209; 356/30
[51] Int. Cl.² ........................................ G01N 21/22
[58] Field of Search ............ 356/30, 209, 210, 215; 250/571, 572

[56] References Cited
UNITED STATES PATENTS 3,819,913  6/1974  Carter et al. ..................... 356/39

OTHER PUBLICATIONS

McCartney et al., "Determination of Proportions of Coal Components by Automated Microscopic Reflectance Scanning", *FUEL*, vol. 50, No. 3, 1971, pp. 226–235.

*Primary Examiner*—John K. Corbin
*Assistant Examiner*—R. A. Rosenberger
*Attorney, Agent, or Firm*—Watson Leavenworth Kelton & Taggart

[57] ABSTRACT

A method and apparatus for automatically measuring the distribution of reflectance of coals is given, which comprises the steps of vertically projecting light to samples of coals on a movable stage, allowing a photodetector to receive said light through a microscope as the stage moves, thereby measuring the reflectance of the samples at a great number of points to obtain the distribution of reflectance, and determining the property of the coals from this distribution of reflectance.

6 Claims, 6 Drawing Figures

FIG. 1

FIG. 2
SAMPLE A

FIG. 3
SAMPLE B

METHOD AND APPARATUS FOR AUTOMATICALLY MEASURING DISTRIBUTION OF REFLECTANCE OF COALS

BACKGROUND OF THE INVENTION

This invention is intended to determine the property of coals in a simple and expedite manner by measuring the distribution of reflectance of the coals.

The term "coals" herein used includes a coal ranging from brown coal to anthracite; a solid hydrocarbon derived from the material of the coal or petroleum system; and carbonized remains of fossil plants contained in a sedimented rocks; and the like.

The coals will change to various hydrocarbon compounds, depending upon the material from which they originate and by the metamorphism action of heat, pressure and time. As a result, they will have various properties. In an attempt to measure this change quantitatively, it has been proposed to measure the content of C, H and O by elementary analysis or to measure the volatile matter by approximate analysis.

However, a natural coal or a solid hydrocarbon technically derived therefrom is generally a mixture of the various compounds, and it is thus difficult to grasp the property of such coals based only upon the average value of analysis.

Recently, an attempt has been made to measure the optical reflectance of coals to overcome the above disadvantage. It is based on the fact that some particular component in the coals has a property to increase the optical reflectance in proportion to the degree of metamorphism, and that the degree of the metamorphism or coalification can thus be determined by measuring the optical reflectance of the particular component.

To know the degree of coalification is not only significant to judge the coking property of the coking coal in coke industry but also helpful in studying correlation of strata in geology or prospecting petroleum by measuring the degree of metamorphism given to strata.

In measuring the reflectance of coals for the above purpose, it has heretofore been a practice to use a photometer attached to a microscope and manually operate the same. Generally, the natrual coals include many kind of hydrocarbons. It is therefore more significant to know the distribution of reflectance rather than to measure the reflectance per se, which will necessitate measuring of reflectance at as many points as possible. Such measuring by manual operation needs a great deal of time and labor, so that the measuring at only 50 to 100 points in one sample has been the maximum. It is of course not sufficient to give a satisfactory result in a practical use. For example, in judging the coking property of the coal, it has heretofore been a practice to conduct such measuring at 50 to 100 points by first carring out the Maceral analysis and then measuring the number of the Vitrinit part in the sample. It takes a lot of time and labor as mentioned above and is thus not efficient. Consequently, an automatic measuring device has been developed to improve accuracy and cut labor by increasing the measuring speed and the number of the measuring points. However, in view of the fact that the reflectance of the coals is as small as about 1% of the incident light thereto and that a clear solution has not been made yet as to the relation between the distribution of the reflectance of the coals and the property thereof, etc., a completely satisfactory apparatus has not been obtained yet, although it is still quite important to know such property of the coals.

For example, in an iron making industry, a great deal of coke is used. In this case, it is extremely useful for presuming the strength of the product coke to judge the coking property of the material coal. It is particularly necessary, where various material coals are imported from various countries, such as in the iron making industry in Japan, for investigation of the quality of the coal imported from the undeveloped coal mine for quality control of the coal imported, or for optimum coal blend, etc. Conventionally, many tests such as approximate analysis, elemental analysis, measuring of fluidization, test as to softening and expanding, measuring of coefficient of bonding power and so on have been proposed, all of which have proved to be insufficient for the practical operation. Furthermore, coking in the test furnace or testing in the practical oven, etc. have been conducted with a lot of time and labor, but a satisfactory result could not be obtained. Under these circumstances, a theory based upon the coal structure that there is a possibility of presuming the strength of the coke by the analysis of the petrographical constituents of the coal and by the measuring of the reflectance of the Vitrinit in the coal has recently been proposed, a part of which has been practised in various countries. This method is being utilized for the investigation of the quality of the coal of the undeveloped coal mine or for the quality control of the coal imported, since it has advantages that the coking property of the coal can be determined with small amount of samples, that the strength of the coke given when many kind of material coals are mixed can be calculated, and that the oxidized coal and the mixed coal can be discriminated, etc. Based upon the theory of the coal histology, the main factor upon which the strength of the coke depends is considered to be (a) the ratio of the component which will melt to the component which will not melt and (b) the bonding power of the component which will melt, when the coke is produced by dry distillation of the coal. It is also known that the bonding power varies with the degree of coalification of a coal can be reasonably expressed in term of the reflectance of the Vitrinit which is the chief component of the coal. It has conventionally been practised, however, to discriminate the components of the coal by the visual power of the operator depending upon its reflectance, optical anisotropy, optical property such as form, hardness, etc. to measure 500 points or more by the point count method and measure 100 points or more of the maximum reflectance of the Vitrinit component in the coal. As a result, it takes about three hours to measure one sample, which is not efficient and gives rise to incur personal errors resulting from the visual operation of the operator.

Accordingly, the value of the strength of the coke derived from the above result is not always reliable. In other words, this method is theoretically correct but the result obtained is not always correct for the reasons that the sample error is unavoidable because of limitation of the number of measuring points and that the personal error is also unavoidable because of the subjectivity of the operator who effects the visual observation by microscope.

Table 1

The petrographical analysis compared with the automatic and manual method

| Sample | Joint Test by domestic eight companies | | | Test by I.C.U.P. 28 companies | | Manual Test | |
|---|---|---|---|---|---|---|---|
| | Max. % | Min. % | Average % | Average % | Deviation % | I% | II% |
| Sample A | | | | | | | |
| Vitrinit | 79.5 | 61.5 | 68.4 | 68.6 | 6.3 | 70.8 | 69.2 |
| Exinit | 16.2 | 10.1 | 13.3 | 12.2 | 6.4 | 9.2 | 10.8 |
| Inertinit | 19.4 | 14.3 | 16.1 | 17.0 | 2.7 | 17.8 | 17.8 |
| Mineral Matter | 2.6 | 2.1 | 2.2 | 2.1 | 1.2 | 2.2 (0.6) | 2.2 (0.6) |
| Mean Reflectance (*525) | 0.78 | 0.73 | 0.75 | 0.76 | 0.03 | | |
| Mean Reflectance (*546) | | | | 0.66 | 0.05 | 0.67 | 0.68 |
| Sample B | | | | | | | |
| Vitrinit | 65.5 | 45.1 | 53.0 | 48.7 | 7.7 | 55.3 | 53.3 |
| Exinit | 3.6 | 0 | 0.8 | 0.3 | 0.9 | 0.6 | 0.5 |
| Inertinit | 49.5 | 29.8 | 41.5 | 47.2 | 7.9 | 40.0 | 42.0 |
| Mineral Matter | 5.4 | 3.0 | 4.1 | 3.8 | 2.0 | 4.1 (0.1) | 4.1 (0.1) |
| Mean Reflectance (*525) | 1.38 | 1.24 | 1.30 | 1.29 | 0.05 | | |
| Mean Reflectance (*546) | | | | 1.15 | 0.05 | 1.15 | 1.15 |
| Sample C (A30% + B70%) | | | | | | | |
| Vitrinit | 65.8 | 53.2 | 59.4 | 57.6 | | 56.6 | 50.7 |
| Exinit | 6.7 | 2.8 | 4.7 | 4.6 | | 2.8 | 6.1 |
| Inertinit | 37.6 | 25.7 | 31.7 | 33.9 | | 36.4 | 39.0 |
| Mineral Matter | 4.5 | 3.9 | 4.2 | 3.9 | | 4.2 | 4.2 |
| Mean Reflectance (*525) | 1.20 | 1.08 | 1.12 | 1.12 | 0.04 | | |
| Mean Reflectance (*546) | | | | 0.98 | 0.03 | 1.00 | 0.98 |

Note:
(1) Figures parenthesized are amount of pyrite included.
(2) *is wave length ($\mu$m) of filter.

Table 1 shows the result of tests conducted at 28 places in the world regarding the same three samples. From this it can be observed how the measuring error is large.

In order to overcome the above defect, the automatic operation of the analysis of the structure has been proposed. For example, there have been developed a method to determine the ratio of each component in a coal by strictly dividing the voltage issued from the photoelectric tube attached to the microscope by utilizing the phenomenon that said structual components have respectively increased reflectances in the order of Exinit, Vitrinit, Inertinit and Pyrite, and a method to cause the computer to memorize directly the output issued from the photoelectric tube attached to the microscope so as to automatically measure the coking property based on the average value of said output by utilizing the phenomenon that the reflectance of the coal changes as the degree of coalification of the coal progresses, etc.

Examples of such literatures are (1) "Determination of proportions of coal components by automated microscopic reflectance scanning" by J. T. McCartney et al in Fuel, Vol. 50 (1971) p226 to 234 and (2) "The development of automatic analysis equipment at the coal research establishment of the national coal board" by J. A. Harrison et al in Proceeding of the Conference on Laboratory Automation I.E.R.E., London, Nov. (1970) 345 page.

However, these methods mentioned above may be useful to a particular kind of coal but are not so adaptable as presuming the coking property of every kind of coals.

The minimal necessary factor for judging the coking property of the coal is to know (a) the degree of coalification of the material coal and (b) the ratio of the component which will melt (hereinafter referred to as "reactives") to the component which will not melt (hereinafter referred to as "inerts") during the coking. Generally, the reflectance of the "inerts," except for its ash value, is higher than that of the "reactives". On the other hand, there is a phenomenon that the reflectance of the "reactives" becomes higher as the degree of coalification progresses. Accordingly, there is considerable difficult caused when the degree of coalification and the amount of the "reactives" are simultaneously determined only by the reflectance. It is because there exist both the "inerts" and the "reactives" in the component having the same reflectance.

DETAILED DESCRIPTION OF THE INVENTION

In view of the above fact, the inventors have made various studies, and developed a measuring device which has much more accuracy than that of the conventional measuring device for the reflectance, as well as a measuring method for fully utilizing such device and for converting the necessary data from the measured value obtained therefrom.

It is therefore an object of this invention to povide a unique method and apparatus capable of overcoming the above disadvantages which have ben encountered in the prior art.

According to this invention, there is provided a method for measuring the reflectance of the coals which comprises providing a movable sample stage below a microscope, said stage moving stepwise by a predetermined distance at each predetermined time, placing a sample on said sample stage, projecting a light to said sample, allowing a photodetector to receive the reflected light via said microscope, converting the same to an electrical output, allowing said output to enter an integrating unit, repeating the above measuring operation at each movement by said distance of said stage so as to measure the reflectance at quite a lot of points, introducing a signal into a calculation unit, said signal having been accumulated in said integrating unit by the instruction of a control unit capable of controlling the operation of said stage, said calculation unit and a record indication unit, allowing said calculation unit to conduct an operation for measuring the distribution of the reflectance, and allowing the result to enter into said record indication unit so as to indicate the distribution of the reflectance, and an apparatus for carrying out the same.

This invention is further described with respect to the drawings.

Figure 1:
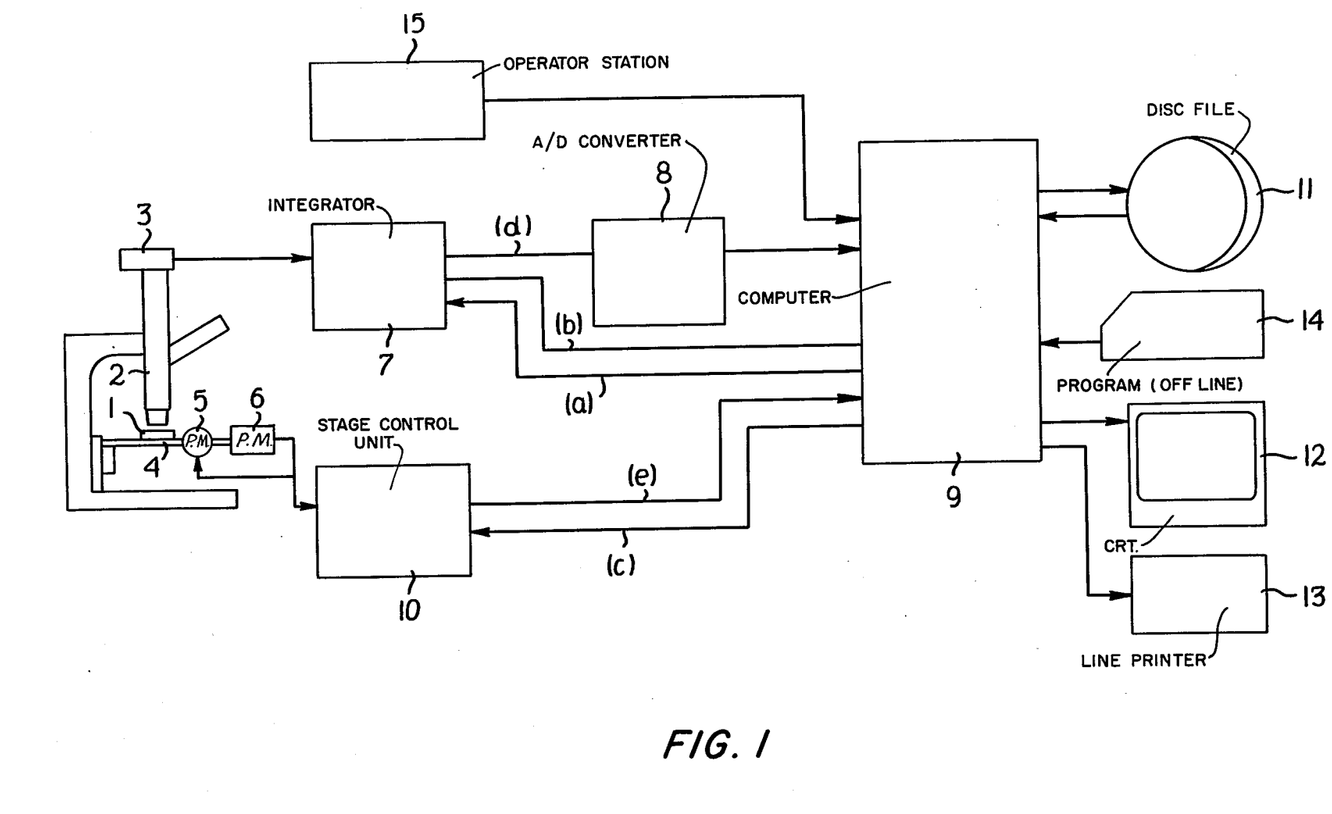
FIG. 1 is a schematic view for explaining one preferable embodiment of this invention.

In FIG. 1, the reference numeral 1 is a sample, and 2 is a microscope. The objective thereof should preferably be an oil immersion type having at least 50 magnification. On the top of the microscope, there is a photomultiplier 3 mounted as the photodetector. The numeral 4 is a movable sample stage capable of moving in the longitudinal and lateral directions in a horizontal plane by means of two step motors 5 and 6. 7 is an integrator or integrating unit connected to said photomultiplier, the output side of which is connected to an AD converter 8 and a computor or calculation unit 9. In the AD converter, the analog signal is converted into the desital value at 10/513 V unit. To the step motors 5, 6, a moving stage control circuit or unit 10 is connected so as to control the operation of the motors 5, 6. In the circuit 10, the width of the step and the number of steps in X-Y axis are set The circuit 10 is in turn connected to the computor 9. The numerals 11, 12 and 13 are record or indication device or unit connected to the computor 9, in which the 11 is a disc file for the measuring result, the 12 is an indication unit C.R.T. for describing the measured amount line, the distribution chart, etc. and the 13 is a line printer for describing the calculation result. The numeral 14 is a program (off line) for calculating the measuring result, and 15 is an operator's box for instructing the measuring condition.

In the practice of this invention for measuring the coking degree of the material coal, a sample of the material coal to be measured is prepared. The preparation of the sample may be done by any known method such as a method of A.S.T.M. D2797, etc. In this case, it is preferable to use one one in which the reflectance of the binder is not more than 0.02% in case of oil immersion and to effect pulverization so as not to produce fine particles of 20 μm or less, or to remove fine particles, if produced.

The sample 1 thus produced is placed on the stage 4 and irradiated from a light source not shown. As the light source, it is preferable to use a tungsten filament or Xenon lamp, etc. of not less than 60 W brightness. Thus, a light having a diameter of 5 μm or less should preferably be projected to the sample 1, and its reflected light is received by the photomultiplier 3. In the conventional method, an electric signal which generates instantaneously from the photoelectric tube is caused to be memorized in this case, but an extremely small amount of light can not accurately be caught owing to the noize coming from the photoelectric tube. In this invention, however, by virtue of the operation of the moving stage control circuit, the step motors 5, 6 are controlled so as to stop the measuring point for about 10 to 100 milliseconds, mostly about 20 to 50 milliseconds, whereby the output of the photoelectric tube for that time is integrated by the integrator 7 and further the noize is removed by an electric filter so that a signal having the S/N ratio of not less than 100 is led to the computer 9. When the measuring at one point is completed like this, the moving stage control circuit 10 is actuated by a signal coming from the computer 9 according to a predetermined program whereby the stepmotors 5, 6 are operated accurately move the sample 1 in the longitudinal and lateral directions by each 10 to 100 μm so that the next measuring point is set within the visual field of the microscope for measuring the reflectance as above. This operation is conducted by a predetermined number of measuring in the measuring area which has preliminarily been set. As the number of the measuring points increases, the accuracy is enhanced. Normally, the object can be accomplished if it reaches at least ten thousand points. In this case, the operation of the computer 9 is as follows:

a. Send a signal to the integrator 7 for instructing start of integration.

b. Receive a signal from the integrator for informing completion of integration.

c. Send a signal to the moving stage control circuit 10 for instructing start of stepping (moving a sample).

d. Receive and memorize a measuring signal from the integrator via the A/D converter 8.

e. Receive a signal from the circuit 10 for informing conpletion of stepping or completion of moving a sample.

The measuring value thus integrated and memorized in the computer 9 is converted into the absolute value of the reflectance which has preliminary been set according to the standard sample, and then indicated in the line printer 13, the indication unit 12, etc. From this result, the strength of the coke can be measured.

In this case, it sometimes happens that extremely fine powders of several micron or less are mixed in the sample and that end parts of the coal particles are measured and the mean reflectance with binders for fixing the sample is included. These things must be eliminated as background. As the Vitrinit has generally the optical anisotropy, it may be measured deviating from the maximum reflectance foward the lower side than that. It is thus necessary to correct the distribution of the reflectance depending upon the degree of the anisotropy preliminarily known. It is natural that any scar or dust on the surface of the sample should be removed since it gives rise to an error in the measuring operation.

The theoretical basis for this invention is described hereinbelow.

In this invention, the reflectance of the sample is measured at a great many points; the distribution of the reflectance is determined; the amount of the melting component and that of the non-melting component in the coking are quantitatively measured according to said distribution of the reflectance; the reflectance of the melting component is determined; and the coking property of the sample is measured.

The "reactives" are relatively uniform components having the main constitution called Vitrinit, and show an almost constant distribution of the reflectance in the same coal layer. On the other hand, the "inerts" have features not only that has a wide distribution of brightness but also that it has many cracks and, pores and that it has hardness, showing outstanding protrusions or hollows on the polished surface. Accordingly, when a curve for distribution of the reflectances is plotted by measuring the reflectance of the whole structural components very accurately and at many points, it can be observed that the Vitrinit component shows a distribution curve similar to the very smooth normal distribution while the "inerts" component shows irregular distribution on the side of high reflectance. It is therefore possible from these dstribution curves to discriminate the "inerts" component easily from the "reactives" component, and at the same time, to know the coking property of the sample, provided that the reflectance of the "reactives" is determined.

It is thus possible with respect to the ordinary coal to convert the data necessary for predicting the coking property by statistic means from the distribution of the reflectance. This is, however, impossible with respect to the coal obtained by mixing various kind of coals, and the following measuring method is effected for that.

When the distribution of the reflectance is measured, the points with quite close distance such as about 10 $\mu$m and those with relatively remote such as about 100 $\mu$m distance are alternately measured. Only the measuring values, of which the difference of the reflectance between the two close points is not more than 0.025%, is recorded independently to obtain the distribution of the reflectance. This can be considered as the distribution of the reflectance of only Vitrinit, since only Vitrinit is very uniform and is the main constitution of the coal.

Figure 5:
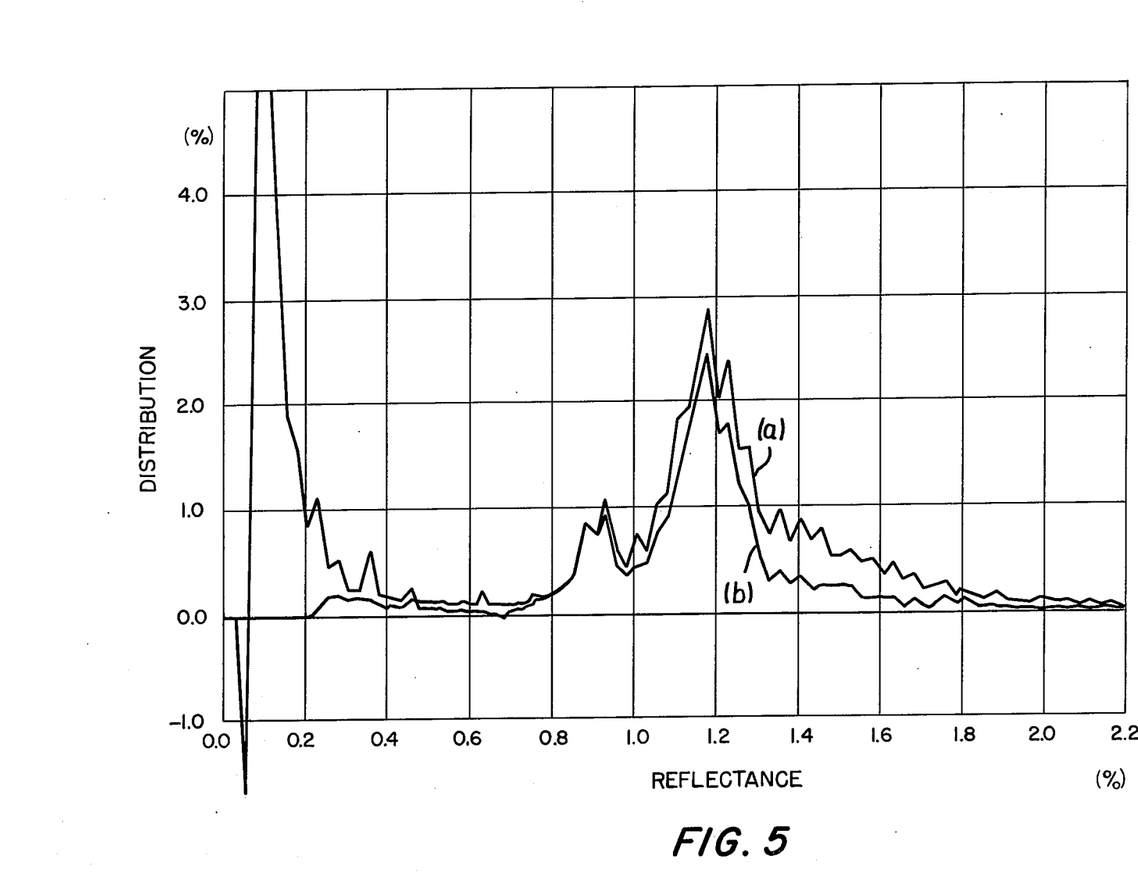
Figure 6:
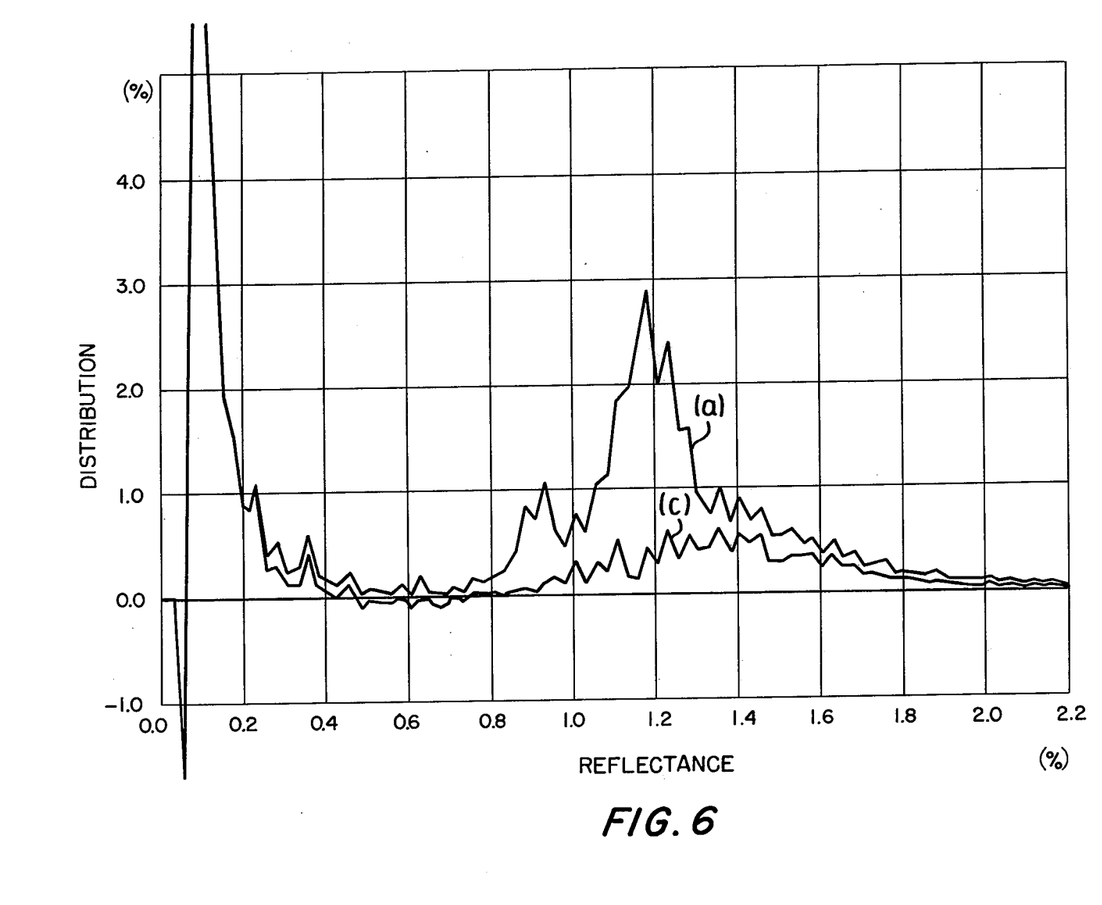

The system of this invention has a program such that the distribution of the reflectance of the whole coal sample and the reflectance of only Vitrinit can be simultaneusly determined in one measuring and the amount of "inerts" can easily be calculated from the difference between the above two. As an example, a distribution (a) of reflectance of mixed coals and a distribution (b) of reflectance of only Vitrinit plotted simultaneously therewith are shown in FIG. 5, and the distribution (a) and a distribution (c) of reflectance of "inerts" obtained by subtracting the (b) from the (a) are shown in FIG. 6.

A measuring result according to this invention is shown below as compared with that of a conventional manual method.

EXAMPLE

Figure 2:
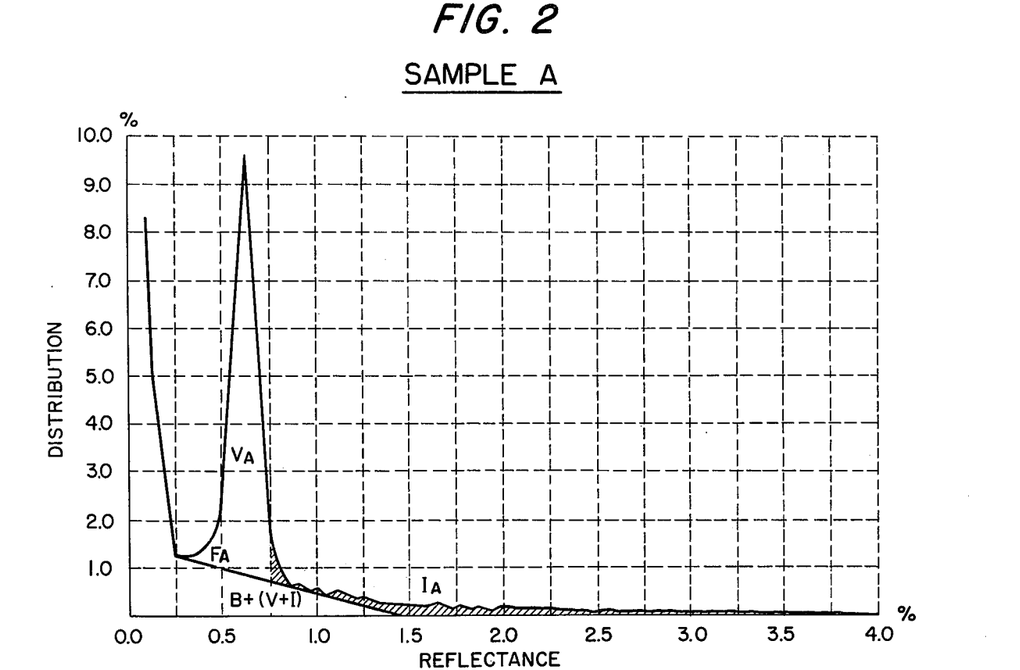
FIGS. 2 to 6 are graphs illustrating examples of measuring results according to this invention.
Figure 3:
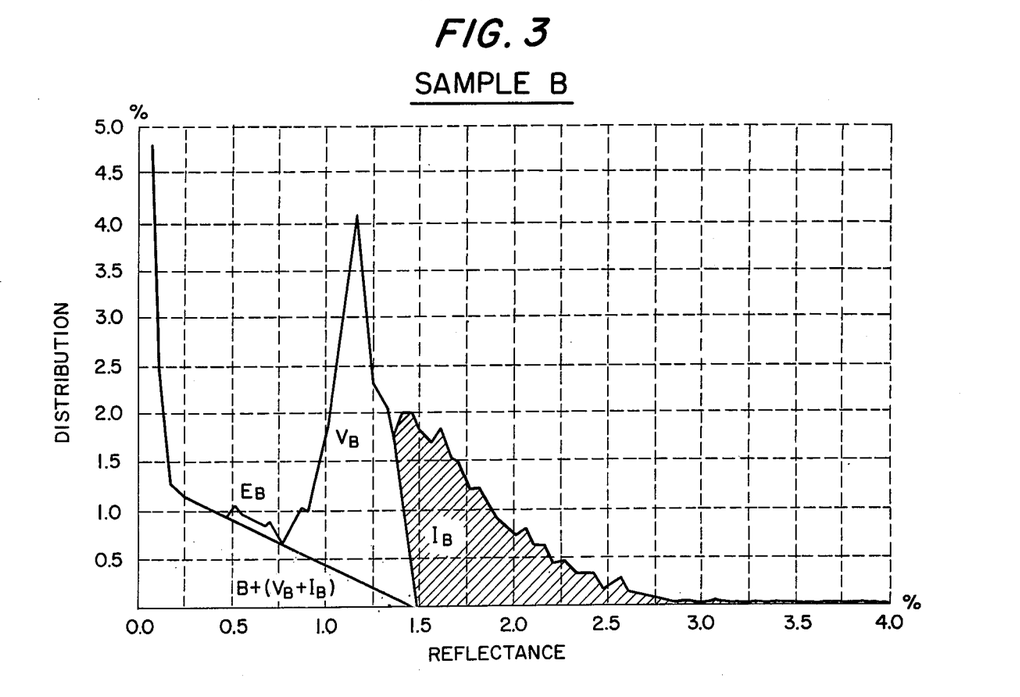
Figure 4:
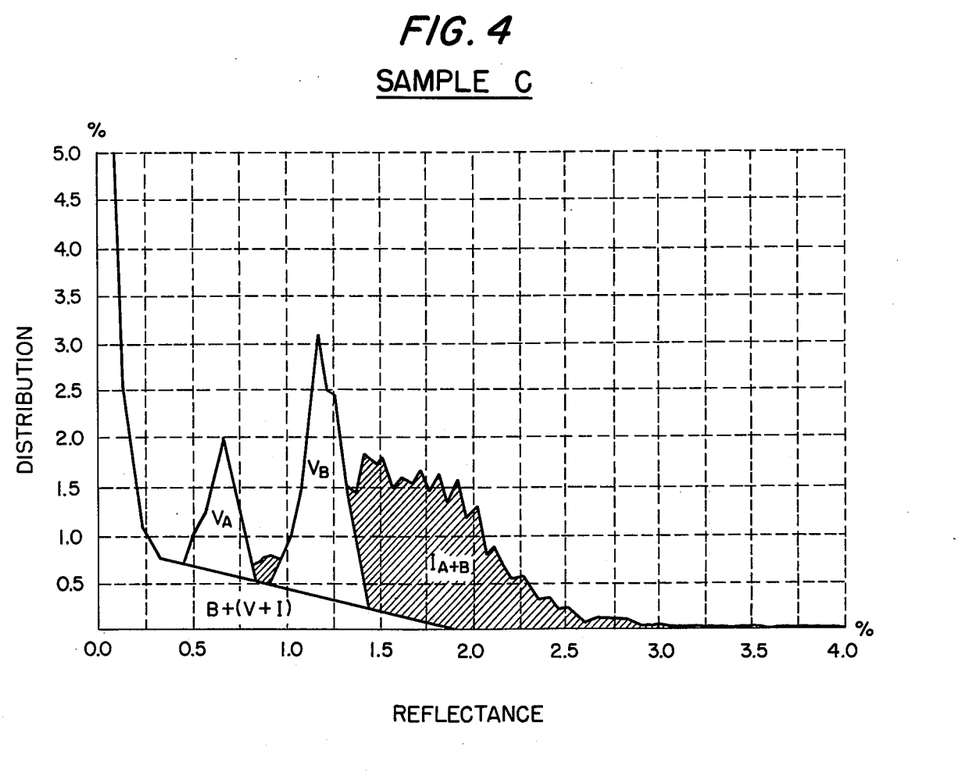

The measuring results of weak caking coal (Sample A), strong caking coal (Sample B) and mixed coals of the two (3:7) (Sample C) are shown in FIGS. 2 to 4 in terms of the distribution of the reflectance. In each Figure, VA and VB are Vitrinit; IA, IB, and $I_{A+B}$ are "inerts" component; B is a binder; and EA and EB are Exinit.

The measuring points are ten thousand per each sample and the measuring time is about 12 minutes per one sample. This distribution indicates the amount of distribution at each 0.05% of the reflectance in terms of 100%.

In these Figures, the binder part [B], the fine particles of several $\mu$m or less in the sample and the part [B +(V + I)] in which measuring points exist in the boundary between the binder and the sample, etc. are excepted.

It is obvious from the results that the main consititution, Vitrinit or VA, VB or $V_{A+B}$ shows almost regular distribution similar to the normal distribution in each sample, while the "inerts" component, IA, IB or $I_{A+B}$ shows irregular distribution over wide area, so that the boundary between the two can easily be discriminated. Moreover, as the size of the reflectance of VA can be measured at the same time, the coking property of the sample can be determined from these data. These measuring results show the same tendency as the conventional one as shown in Table 1.

This invention is further described with respect to the use in the oil prospecting.

One method to determine as to whether or not the oil is buried has recently reported that when the reflectance of a sample of the carbonaceous material in the accumulated coal is 0.6 or less there will be no oil, while when it is 1.4 or more it only exists in a gaseous state. Accordingly, in measuring the distribution of the reflectance of a sample as in the case of coal, it can be judged that when the peak of the distribution of the reflectance is 0.6 or less, there is no oil, while when it is 1.4 or more, there is only a gas, and that only when the peak thereof exists between 0.6 and 1.4 an oil value exits therein.

By measuring, in this way, (a) the coking degree of a coal or a solid hydrocarbon derived from coal or oil material or a carbonized plant remains contained in deposited rocks and (b) the components therein, it is possible (1) to rapidly judge the coking property of the various coals, (2) to check the change of quality of the coals for utilizing it in control or maintenance of the coal, (3) to effectively carry out control or maintenance of mixing the coal to be charged into a coke oven, and (4) to determine the degree of coalification of the coals in the deposited rocks and utilize it in the prospecting of oil.

As set forth hereinabove, this invention is intended to replace the conventional visual measuring by the unique automatical operation for all steps. Accordingly it has great advantages that there is no personal error caused and yet a very rapid measuring can be done as compared with the prior art, etc.

We claim:

1. A method for measuring the reflectance of the coals wich comprises providing a movable sample stage below a microscope, said stage moving stepwise by a predetermined distance at each predetermined time, placing a sample on said sample stage, projecting light onto said sample, conducting light reflected by said sample to a photodetector via said microscope for converting said reflected light to an electrical output, integrating said output, repeating the above measuring operation at each such movement of said stage so as to measure the reflectance at a large plurality of points, introducing into a calculation unit outputs accumulated in said integrating unit by the instruction of a control unit controlling the movement of said stage, said calculation unit and a record indication unit, said calculation unit conducting an operation for measuring the distribution of the reflectance, and displaying the results of such calculation unit operation so as to indicate the distribution of the reflectance.

2. A method according to claim 1 in which the reflectance of the sample to be measured is measured at 10,000 points or more with predetermined distance and the distribution of that reflectance is measured.

3. A method according to claim 1 for predicting the coking property of the coals by determining the distribution of the reflectance, which comprises measuring quantitatively the "reactives" and the "inerts" based on the respective reflectance characteristics and also determining the reflectance of the "reactives".

4. An apparatus adapted for use in automatically measuring the reflectance of coals which comprises a photodetector mounted to receive light from a microscope for converting the reflected light from a sample via said microscope to an electric output, a sample stage mounted below said microscope, means for moving said sample stage in longitudinal and lateral directions by predetermined distances, an integrating unit connected to said photodetector for integrating such electric outputs, a calculation unit connected to said integrating unit for determining reflectance distrubution, a controlling unit for controlling the operations of said sample stage, of said integrating unit and of said calculation unit, and a recording indication unit for recording the distribution of the reflectance.

5. An apparatus according to claim 4 in which such moving means move said sample stage stepwise laterally and longitudinally for a predetermined distance in the range of 10 and 100 $\mu$m and stops such movement completely for a measuring time in the range of 5 to 50 ms.

6. A method for measuring the reflectance of the coals which comprises providing a movable sample stage below a microscope, said stage moving stepwise by a predetermined distance at each predetermined time, placing a sample on said sample stage, projecting light onto said sample, conducting light reflected by said sample to a photodetector via said microscope for converting said reflected light to an electrical output, integrating said output, repeating the above measuring operation at each such movement of said stage so as to measure the reflectance at a large plurality of points, introducing into a calculation unit outputs accumulated in said integrating unit by the instruction of a control unit controlling the movement of said stage, said calculation unit and a record indication unit, said calculation unit conducting an operation for mesuring the distribution of the reflectance, and displaying the result of such calculation unit operation so as to indicate the distribution of the reflectance, said predetermined distance in such stepwise movement of said stage being selected from first measures of about 100 $\mu$m and second measures of about 100 $\mu$m, said calculation unit operation involving only those integrated electrical outputs obtained in cases where the difference of the reflectance between adjacent points spaced by such 10 $\mu$m distance is not more than 0.025%, such reflectance distribution thereby being determined as that of "reactives".

* * * * *

UNITED STATES PATENT OFFICE
CERTIFICATE OF CORRECTION

PATENT NO. : 4,030,837
DATED : June 21, 1977
INVENTOR(S) : Kojiro Kojima et al

It is certified that error appears in the above-identified patent and that said Letters Patent are hereby corrected as shown below:

At Col. 1, line 24, "mixture of the" should read --mixture of--.

At Col. 2, line 45, after "coalification" and before "of", insert --and that the degree of coalification--.

At Col. 3, line 52, "structual components" should read --structural components--.

At Col. 5, line 12, "have ben encountered" should read --have been encountered--.

At Col. 7, line 25, "it has hardness" should read --it has a high hardness--.

At Col. 8, line 68, (Claim 1), "coals wich comprises" should read --coals which comprises--.

At Col. 10, line 31, (Claim 6), "of about 100" should read --of about 10--.

Signed and Sealed this

Sixth Day of February 1979

[SEAL]

Attest:

RUTH C. MASON
Attesting Officer

DONALD W. BANNER
Commissioner of Patents and Trademarks